US00PP15435P2

(12) United States Plant Patent
Sjulin et al.

(10) Patent No.: US PP15,435 P2
(45) Date of Patent: Dec. 14, 2004

(54) STRAWBERRY PLANT NAMED 'DRISCOLL JUBILEE'

(50) Latin Name: *Fragaria×ananassa*
Varietal Denomination: Driscoll Jubilee

(75) Inventors: Thomas M. Sjulin, Aromas, CA (US); Joseph T. DeRuse, Almeria (ES); JoAnne Coss, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 10/619,689

(22) Filed: Jul. 15, 2003

(51) Int. Cl.[7] ..... A01H 5/00
(52) U.S. Cl. ..... Plt./209
(58) Field of Search ..... Plt./209, 208

*Primary Examiner*—Anne Marie Grunberg
*Assistant Examiner*—June Hwu
(74) *Attorney, Agent, or Firm*—Jones Day

(57) ABSTRACT

This invention relates to a new and distinct variety of strawberry named 'Driscoll Jubilee.' The variety is similar to the varieties 'Driscoll Camarillo' and 'Driscoll Coronation.' The variety is distinguished from 'Driscoll Camarillo' and 'Driscoll Coronation,' in particular, by its smaller spread of plant, conic shaped fruit of greater length than width, thinner stolons, red and white internal fruit color, the shape of the base of the terminal leaflets is acute, and the inflorescence is beneath the foliage.

5 Drawing Sheets

Latin name of the genus and species of the plant claimed: The variety is botanically identified as *Fragaria×ananassa.*

Variety denomination: The strawberry variety denomination is 'Driscoll Jubilee'.

1. BACKGROUND OF THE INVENTION

The new variety originated as a result of a controlled cross between the strawberry plants '50C130' (unpatented variety) and '19A331' (unpatented variety) in an ongoing breeding program, and was discovered as a seedling in Kent, England in 1999. The original seedling of the new cultivar was asexually propagated by stolons in a Nursery in Kent, England. Propagules were transplanted to a controlled breeding plot in Monterey, Calif., where the variety was identified and selected for further evaluation. 'Driscoll Jubilee' was subsequently asexually propagated and underwent further testing in Monterey, Calif. for one year. This propagation and testing has demonstrated that the combination of traits disclosed herein which characterize the new variety are fixed and retained true to type through successive generations of asexual reproduction.

2. SUMMARY OF THE INVENTION

The present invention relates to a new and distinct variety of strawberry named 'Driscoll Jubilee.' The variety is botanically identified as *Fragaria×ananassa.* The new variety is distinguished from other varieties by a number of characteristics as set forth in Tables 1–4.

3. COMPARISON TO SIMILAR VARIETIES

The varieties which we believe to be similar to 'Driscoll Jubilee' from those known to us are 'Driscoll Camarillo' (U.S. Plant Pat. No. 14,771) and 'Driscoll Coronation' (U.S. Plant patent application Ser. No. 10/619,692). These are several characteristics of the new variety that are different from, or not possessed by 'Driscoll Camarillo' and 'Driscoll Coronation'. The new variety has a smaller spread of plant, conic shaped fruit of greater length than width, thinner stolons, red and white internal fruit color, the shape of the base of the terminal leaflets is acute, and the inflorescence is beneath the foliage. The internal fruit color of 'Driscoll Jubilee' and 'Driscoll Camarillo' comprises a white color interspersed in a striped manner among the orange-red or red color described for each variety. Each color described for the internal fruit color of 'Driscoll Camarillo' and 'Driscoll Jubilee' is individually present in the internal fruit tissues. In contrast, the internal fruit color of 'Driscoll Coronation' is whitish.

'Driscoll Jubilee' is distinguished from its maternal parent '50C130' by its smaller fruit size, firmer flesh, and its fully everbearing habit. 'Driscoll Jubilee' is distinguished from its paternal parent '19A331' by its redder external fruit color, firmer flesh, and sweeter taste.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

5. DESCRIPTION OF THE NEW VARIETY

Figure 1:
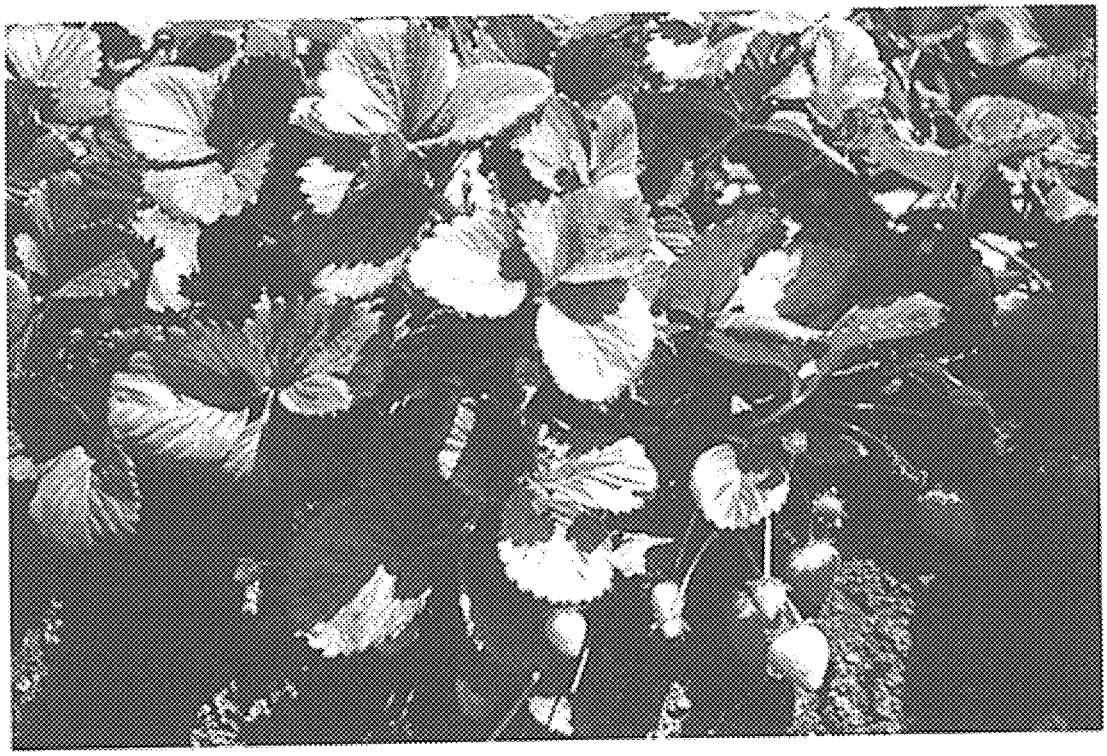
FIG. 1 shows the whole the plant.
Figure 2:
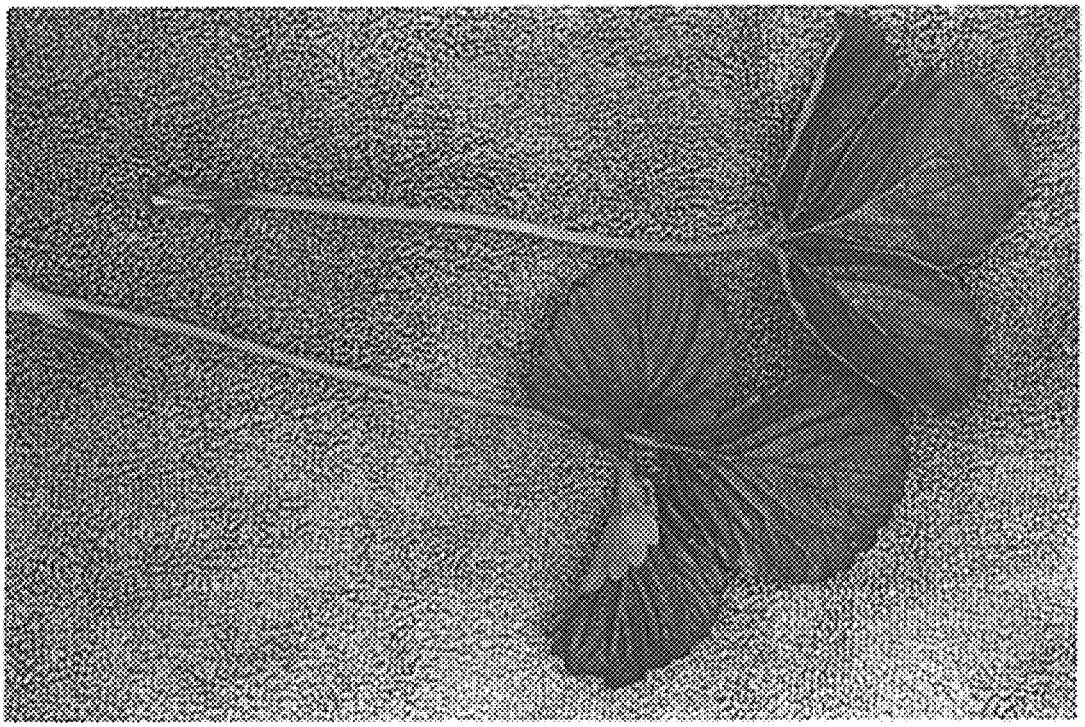
FIG. 2 shows the upper side of the leaves of the plant.
Figure 3:
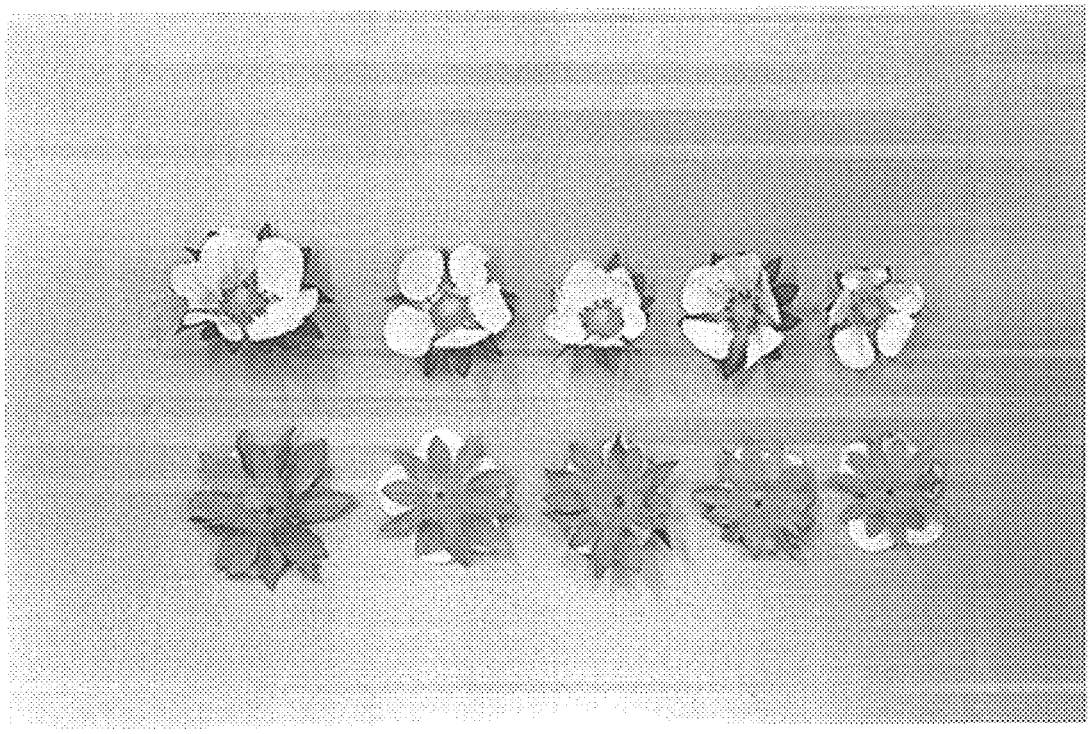
FIG. 3 shows the upper side and underside of the flowers.
Figure 4:
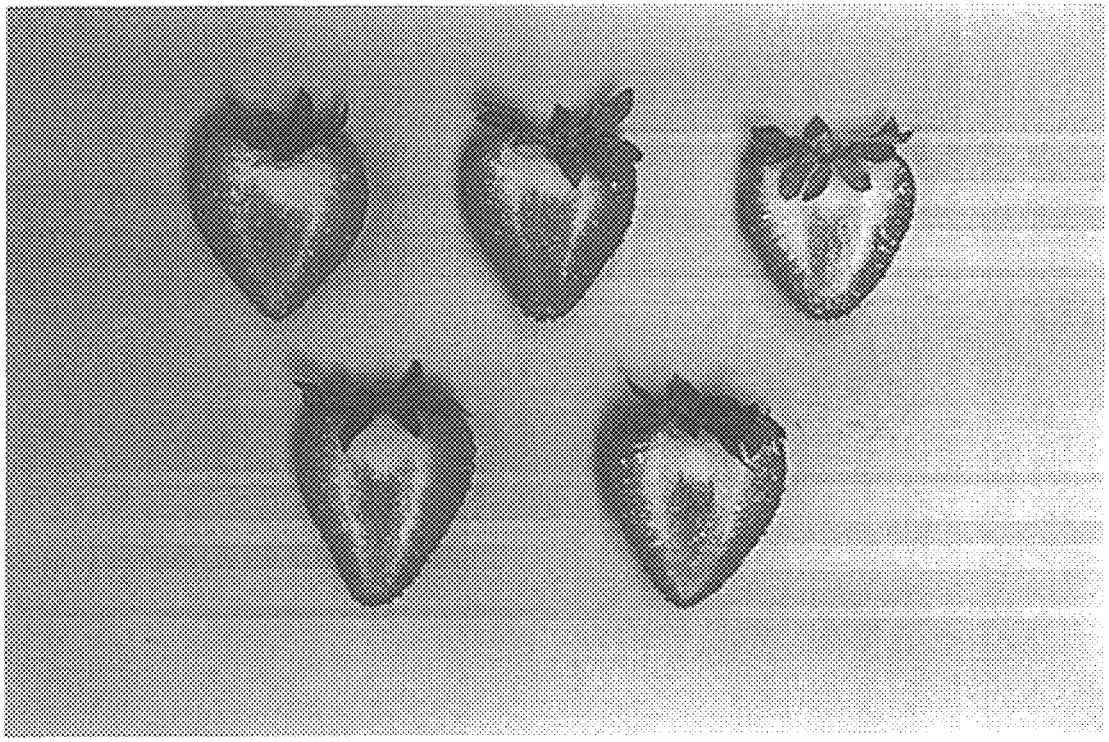
FIG. 4 shows the fruit in longitudinal cross-section.
Figure 5:
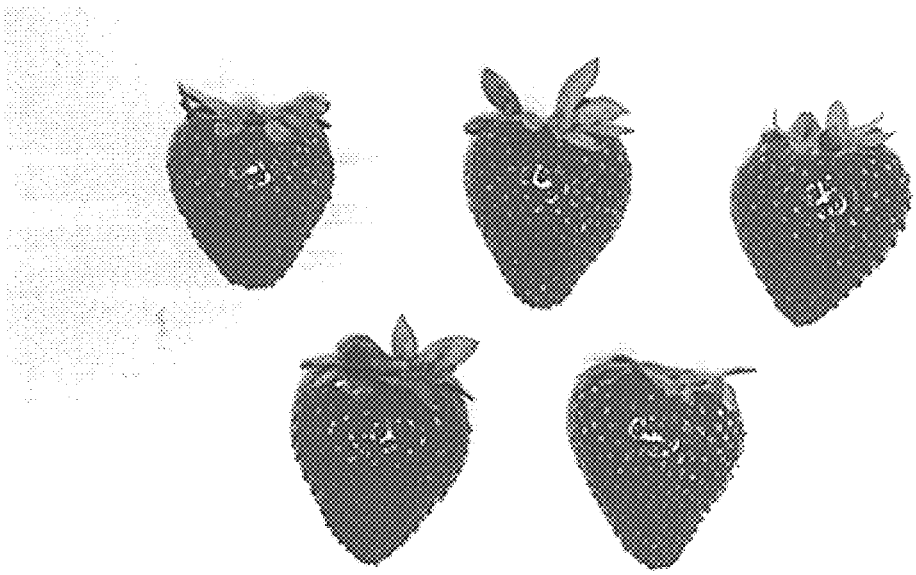
FIG. 5 shows a close-up of the fruit.

The following detailed description of the new variety is based upon observations taken of plants and fruit grown in Monterey County, Calif., U.S.A. This description is in accordance with UPOV terminology. Observations of 'Driscoll Jubilee', 'Driscoll Camarillo' and 'Driscoll Coronation' were taken in side by side comparison in the year 2002. Plants for observation were harvested from a low elevation nursery in Tehama County, Calif. in December 2001, and held in refrigerated storage until planting in Monterey County, Calif. in March 2002. Plants were grown in raised beds of soil under conditions typical of commercial strawberry production along the central coast of California. Fruits were harvested twice weekly for yield determination from May to October 2002. Measurements of plant, flower, and fruit characteristics were made in August 2002, approximately five months after planting. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

5.1 PROPAGATION

The new variety is principally propagated by way of stolons. Although propagation by stolons is presently preferred, other known methods of propagating strawberry plants may be employed.

5.2 CHARACTERISTICS OF THE NEW VARIETY

Information on the new variety is presented in Tables 1, 2, 3 and 4. In the tables, the flowers described are secondary flowers except where indicated. The fruit described is the secondary fruit on five month old plants. Fruit and flower measurements are an average of both primary and secondary fruit and flowers.

Table 1 provides information on the plant and fruit characteristics of the new variety 'Driscoll Jubilee' compared with characteristics of 'Driscoll Camarillo' and 'Driscoll Coronation.' Table 2 provides additional information of the plant and fruit characteristics of the new variety 'Driscoll Jubilee' compared with characteristics of the varieties 'Driscoll Camarillo' and 'Driscoll Coronation.' Table 3 provides reactions of the new variety to stresses, pests and diseases compared with reactions of the varieties 'Driscoll Camarillo' and 'Driscoll Coronation.' Table 4 provides isozyme characteristics of the new variety as compared to that of the varieties 'Driscoll Camarillo' and 'Driscoll Coronation.'

TABLE 1

QUANTITATIVE COMPARISON OF 'DRISCOLL JUBILEE', 'DRISCOLL CAMARILLO,' AND 'DRISCOLL CORONATION'

| | 'Driscoll Jubilee' | 'Driscoll Camarillo' | 'Driscoll Coronation' |
|---|---|---|---|
| Plant Characteristics | | | |
| Height of plant (cm) | 18.3 | 20.5 | 17.0 |
| Spread of plant (cm) | 30.7 | 39.4 | 33.2 |
| Number of crowns | 3.5 | 3.0 | 3.0 |
| Leaf Characteristics | | | |
| Terminal leaflet length (cm) | 6.9 | 8.4 | 7.9 |
| Terminal leaflet width (cm) | 6.7 | 8.5 | 7.4 |
| Terminal leaflet length/width ratio | 1.04 | 0.99 | 1.07 |
| # Teeth/terminal leaflet | 20.1 | 27.0 | 24.3 |
| Color of upper side | 147A dark green | 147A dark green | 147A dark green |
| Color of under side | 138B light to medium green | 147C light green | 139C light to medium green |
| Petiole length (cm) | 15.8 | 16.8 | 16.2 |
| Petiole color | 145A | 145A | 145A |

TABLE 1-continued

QUANTITATIVE COMPARISON OF 'DRISCOLL JUBILEE', 'DRISCOLL CAMARILLO,' AND 'DRISCOLL CORONATION'

| | 'Driscoll Jubilee' | 'Driscoll Camarillo' | 'Driscoll Coronation' |
|---|---|---|---|
| Bract frequency | 42% typically double | 67% typically double | 25% typically double |
| Stipule length (cm) | 3.1 | 4.0 | 3.3 |
| Stipule width (cm) | 1.0 | 1.0 | 0.8 |
| Flower Characteristics | | | |
| Petal length (cm) | 1.12 | 1.13 | 0.96 |
| Petal width (cm) | 1.17 | 1.29 | 0.93 |
| Petal length/width Ratio | 0.96 | 0.88 | 1.03 |
| Flower diameter (cm) | 2.92 | 3.17 | 2.55 |
| Calyx diameter (cm) | 2.65 | 3.09 | 2.51 |
| Average Fruiting truss length (cm) | 27.7 | 33.2 | 24.2 |
| Petal color (cm) | 155C | 155C | 155C |
| Fruit Characteristics | | | |
| Fruit length (cm) | 3.8 | 3.8 | 3.9 |
| Fruit width (cm) | 3.4 | 3.9 | 3.9 |
| Fruit length/width ratio | 1.10 | 0.97 | 0.99 |
| Average berry weight (g) | 19.8 | 20.7 | 20.0 |
| External color | 45A red | 42A red | 45B red |
| Internal color | 43A - 155B red and white | 33A - 155C orange red and white | 159D whitish |
| Achene coloration | 184A to 4A | 184B to 4B | 184A to 8B |
| Yield (g/plant) | 600 | 1200 | 850 |

TABLE 2

QUALITATIVE COMPARISON OF 'DRISCOLL JUBILEE', 'DRISCOLL CAMARILLO,' AND 'DRISCOLL CORONATION'

| | 'Driscoll Jubilee' | 'Driscoll Camarillo' | 'Driscoll Coronation' |
|---|---|---|---|
| Plant | | | |
| Habit | flat globose | flat globose | flat |
| Density | open to medium | open | open |
| Vigor | weak to medium | medium to strong | weak to medium |
| Leaf | | | |
| Shape in cross section | slightly concave to flat | concave | slightly concave to flat |
| Interveinal blistering | strong | strong | medium |
| Glossiness | medium | medium to strong | strong |
| Number of leaflets | three only | three only | three only |
| Terminal leaflet margin profile | revolute | revolute | revolute |
| Terminal leaflet shape of base | acute | rounded | obtuse |
| Terminal leaflet shape of teeth | rounded | rounded | obtuse |
| Stipule pubescence | sparse to medium | medium | sparse |
| Petiole pubescence | very sparse | sparse | very sparse to sparse |
| Petiole pose of hairs | outwards to downwards | upwards to outward | outwards |
| Stolon | | | |
| Amount | medium | medium | few to medium |
| Anthocyanin coloration | medium | medium | medium |

TABLE 2-continued

QUALITATIVE COMPARISON OF 'DRISCOLL JUBILEE', 'DRISCOLL CAMARILLO,' AND 'DRISCOLL CORONATION'

| | 'Driscoll Jubilee' | 'Driscoll Camarillo' | 'Driscoll Coronation' |
|---|---|---|---|
| Thickness | thin to medium | thick | medium |
| Pubescence | sparse to medium | medium | medium |
| Inflorescence | | | |
| Position relative to foliage | beneath | above | level |
| Diameter of calyx relative to corolla on secondary flowers | smaller to same size | smaller to same size | smaller to same size |
| Diameter of inner calyx relative to outer on secondary flowers | smaller | same size | smaller |
| Spacing of petals | touching to overlapping | overlapping | touching |
| Fruiting Truss | | | |
| Attitude at first picking | semi-erect | semi-erect to prostrate | prostrate |
| Fruit | | | |
| Predominant shape | conical | chordate | chordate |
| Difference in shapes between primary and secondary fruits | very slight to slight | slight to moderate | slight to moderate |
| Band without achenes | very narrow | very narrow | very narrow |
| Unevenness of surface | very weak | weak to medium | very weak to weak |
| Evenness of color uneven | slightly uneven | even | slightly uneven to even |
| Glossiness | strong | strong | strong |
| Insertion of achenes | level to above | below to level | level |
| Insertion of calyx | in a basin to level | in a basin | in a basin |
| Pose of the calyx segments | spreading | spreading to reflexed | spreading |
| Size of calyx in relation to fruit on secondary fruit | smaller to same size | smaller | same size to larger |
| Adherence of calyx | strong | strong | medium |
| Firmness of flesh | medium to firm | firm | medium |
| Evenness of flesh color | slightly uneven | slightly uneven | even |
| Distribution of flesh color | marginal and central | marginal and central | central |
| Hollow center size | absent to small | absent to small | small to medium |
| Sweetness | medium to strong | medium | strong |
| Texture when tasted | medium | medium | fine |
| Acidity | medium | medium | weak |
| Time of flowering | medium | medium | medium |
| Type of bearing | fully everbearing | fully everbearing | fully everbearing |

5.3 REACTION TO STRESS, PESTS, AND DISEASE

TABLE 3

REACTIONS TO STRESS PESTS AND DISEASES FOR 'DRISCOLL JUBILEE', 'DRISCOLL CAMARILLO,' AND 'DRISCOLL CORONATION'

| | 'Driscoll Jubilee' | 'Driscoll Camarillo' | 'Driscoll Coronation' |
|---|---|---|---|
| Reaction to Stress | | | |
| high pH | moderately resistant | moderately resistant | moderately resistant |
| high soil salt levels | moderately susceptible | moderately resistant | moderately susceptible |
| Reaction to Pests | | | |
| *Tetranychus urticae* | moderately susceptible | moderately susceptible | moderately susceptible |
| *Lygus hesperus* | susceptible | susceptible | susceptible |
| Reaction To Diseases | | | |
| Botrytis fruit rot | moderately susceptible to moderately resistant | moderately susceptible to moderately resistant | moderately susceptible to moderately resistant |
| Powdery mildew | susceptible | susceptible to highly susceptible | moderately susceptible |
| Verticillium wilt | moderately resistant | moderately susceptible | moderately susceptible |

5.4 ISOZYME ANALYSIS

In addition to the morphological description above, the new cultivar 'Driscoll Jubilee' has been analyzed to obtain an indication of its genetic makeup to provide further means for identifying the new variety and distinguishing it from other somewhat similar and/or related strawberry varieties. Specifically, leaf samples of 'Driscoll Jubilee', 'Driscoll Camarillo' and 'Driscoll Coronation' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL JUBILEE,' 'DRISCOLL CAMARILLO,' AND 'DRISCOLL CORONATION'

| Locus | 'Driscoll Jubilee' | 'Driscoll Camarillo' | 'Driscoll Coronation' |
|---|---|---|---|
| PGI | A1 | A2 | A3 |
| LAP | B3 | B3 | B3 |
| PGM | C4 | C4 | C4 |

What is claimed:

1. A new and distinct variety of strawberry plant, substantially as shown and described.

* * * * *